United States Patent [19]

Millar et al.

[11] Patent Number: 5,248,793
[45] Date of Patent: Sep. 28, 1993

[54] PROCESS FOR THE SYNTHESIS OF (4R-CIS)-1,1-DIMETHYLETHYL 6-IODOMETHYL OR 6-(PHENYL-SUBSTITUTED)SULFONYLOXYMETHYL-2,2-DIMETHYL-1,3-DIOXANE-4-ACETATE

[75] Inventors: Alan Millar; Donald E. Butler, both of Holland, Mich.

[73] Assignee: Warner-Lambert Company, Morris Plains, N.J.

[21] Appl. No.: 994,189

[22] Filed: Dec. 21, 1992

Related U.S. Application Data

[60] Continuation of Ser. No. 815,083, Dec. 27, 1991, abandoned, which is a division of Ser. No. 599,521, Oct. 17, 1990, Pat. No. 5,103,024.

[51] Int. Cl.$^5$ ............................................. C07D 319/06
[52] U.S. Cl. .................................... 549/375; 549/373
[58] Field of Search ................................ 549/375, 373

[56] References Cited

U.S. PATENT DOCUMENTS

| | | | |
|---|---|---|---|
| 4,647,576 | 3/1987 | Hoefle et al. | 514/422 |
| 4,681,893 | 7/1987 | Roth | 514/422 |
| 5,003,080 | 3/1991 | Butler et al. | 548/517 |
| 5,093,363 | 3/1992 | Kita et al. | 514/532 |

FOREIGN PATENT DOCUMENTS

| | | |
|---|---|---|
| 0330172 | 8/1989 | European Pat. Off. |
| 0414206 | 2/1991 | European Pat. Off. |
| 0418648 | 3/1991 | European Pat. Off. |

OTHER PUBLICATIONS

Sunay et al., Tetrahedron Letters, 27, No. 44, pp. 5335-5338 (1986).

*Primary Examiner*—Nicky Chan
*Attorney, Agent, or Firm*—Francis J. Tinney

[57] ABSTRACT

An improved process for the preparation of (4R-cis)-1,1-dimethylethyl 6-cyanomethyl-2,2-dimethyl-1,3-dioxane-4-acetate is described where a hydroxy ester derivative is converted in two steps to the desired product, as well as valuable intermediates used in the process.

2 Claims, No Drawings

PROCESS FOR THE SYNTHESIS OF (4R-CIS)-1,1-DIMETHYLETHYL 6-IODOMETHYL OR 6-(PHENYL-SUBSTITUTED)SULFONYLOX-YMETHYL-2,2-DIMETHYL-1,3-DIOXANE-4-ACETATE

This is a continuation of Ser. No. 815,083, filed Dec. 27, 1991, now abandoned; and which is a division of Ser. No. 599,521, filed Oct. 17, 1990, now patent No. 5,103,024.

BACKGROUND OF THE INVENTION (4R-Cis)-1,1-dimethylethyl 6-(2-aminoethyl)-2,2-dimethyl-1,3-dioxan-4-acetate is a key intermediate in the preparation of (2R-trans)-5-(4-fluorophenyl)-2-(1-methylethyl)-N,4-diphenyl]-1-[2-(tetrahydro 4-hydroxy-6-oxo-2H-pyran-2-yl)ethyl]-1H-pyrrol ®-3-carboxamide or the salt of the hydroxy acid, [R-(R*,R*)]-2-(4-fluorophenyl)-$\beta,\delta$-dihydroxy-5-(1-methylethyl) -3- phenyl-4-[(phenylamino)carbonyl]-1H-pyrrole-1-heptanoic acid calcium salt (2:1), corresponding to the opened lactone ring of the aforementioned compound described in U.S. Pat. Nos. 4,647,576 and 4,681,893, which are herein incorporated by reference. The aforementioned compound is useful as an inhibitor of the enzyme 3-hydroxy-3-methylglutaryl-coenzyme A reductase (HMG-CoA reductase) and is thus useful as a hypolipidemic and hypocholesterolemic agent.

(4R-Cis)-1,1-dimethylethyl 6-(2-aminoethyl)-2,2-dimethyl-1,3-dioxane-4-acetate may be, in turn, prepared from (4R-cis)-1,1-dimethylethyl 6-cyanomethyl-2,2-dimethyl-1,3-dioxane-4-acetate.

A synthetic procedure for preparing (4R-cis)-1,1-dimethylethyl 6-cyanomethyl-2,2-dimethyl-1,3-dioxane-4-acetate is disclosed in copending U.S. patent application Ser. No. 303,733. The aforementioned procedure involves a linear synthetic route involving 10 steps, including a low temperature ($-85°$ C. to $-95°$ C.) reaction carried out under carefully controlled conditions. The reaction involves reduction of a hydroxy ketone with sodium borohydride and a trialkylborane. Although this reaction provides the target compound in high enantiomeric excess, it is difficult to conduct on a large-scale and employs expensive reagents which are difficult to handle.

The displacement of sulfonates and halides by cyanide is well known in the art. However, such displacements in complex systems, and in particular a system containing a 1,3-dioxane ring, have not been successfully carried out. In point of fact, Sunay, U. and Fraser-Reid, B., *Tetrahedron Letters*, 27, pages 5335–5338 (1986) reported the failure of such a displacement in a system containing a 1,3-dioxane ring.

Thus, we have surprisingly and unexpectedly found that the nitrile of the present invention, (4R-cis)-1,1-dimethylethyl-6-cyanomethyl-2,2-dimethyl-1,3-dioxane-4-acetate, can be obtained by a process of displacing various activated sulfonate o halide 1,3-dioxane derivatives with a metal cyanide.

The object of the present invention is an improved, short, efficient, and economical process for the preparation of (4R-cis)-1,1-dimethylethyl 6-cyanomethyl-2,2-dimethyl-1,3-dioxane-4-acetate. Thus, the present method avoids the costly, low temperature reaction of the prior method and is amenable to large scale synthesis.

SUMMARY OF THE INVENTION

Accordingly, a first aspect of the present invention is an improved process for the preparation of the compound of Formula I

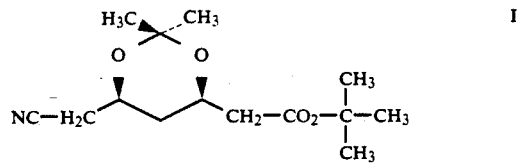

which comprises:
(a) treating the compound of Formula IV

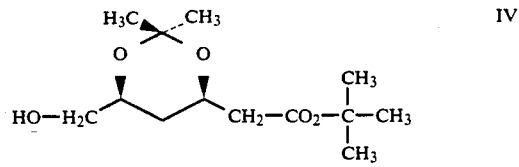

with a compound of Formula V

wherein Ar is aryl; and X is halogen in the presence of a base and a solvent to afford a compound of Formula II

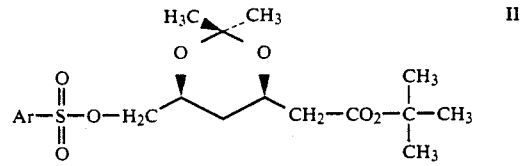

wherein Ar is as defined above; or alternatively
(b) treating a compound of Formula II with an alkali iodide in a solvent at about 0° C. to about the reflux temperature of the solvent to afford the compound of Formula III

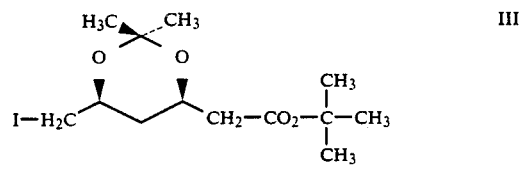

(c) treating a compound of Formula II or the compound of Formula III with a compound of Formula VI

wherein M is an alkali metal, silver or copper (I) in a solvent at about 0° C. to about 100° C. to afford the compound of Formula I.

A second aspect of the present invention is a novel intermediate of Formula

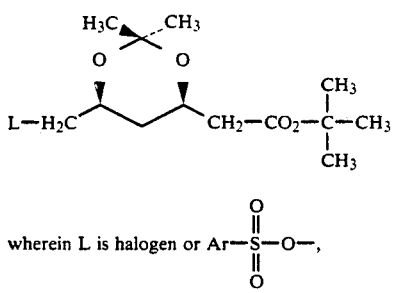

wherein L is halogen or Ar—S(=O)(=O)—O—, wherein Ar is aryl, which is useful in the preparation of the compound of Formula I

DETAILED DESCRIPTION OF THE INVENTION

In this invention, the term "aryl" means an aromatic radical which is a phenyl group substituted by one to two substituents selected from halogen or nitro.

"Halogen" is iodine, bromine, chlorine, and fluorine.

"Alkali metal" is a metal in Group IA of the periodic table and includes, for example, lithium, sodium, potassium, and the like.

The process of the present invention is a new, improved, economical, and commercially feasible method for preparing (4R cis)-1,1-dimethylethyl 6-cyanomethyl-2,2-dimethyl-1,3-dioxane 4-acetate. The process of the present invention is outlined in the following scheme:

SCHEME I

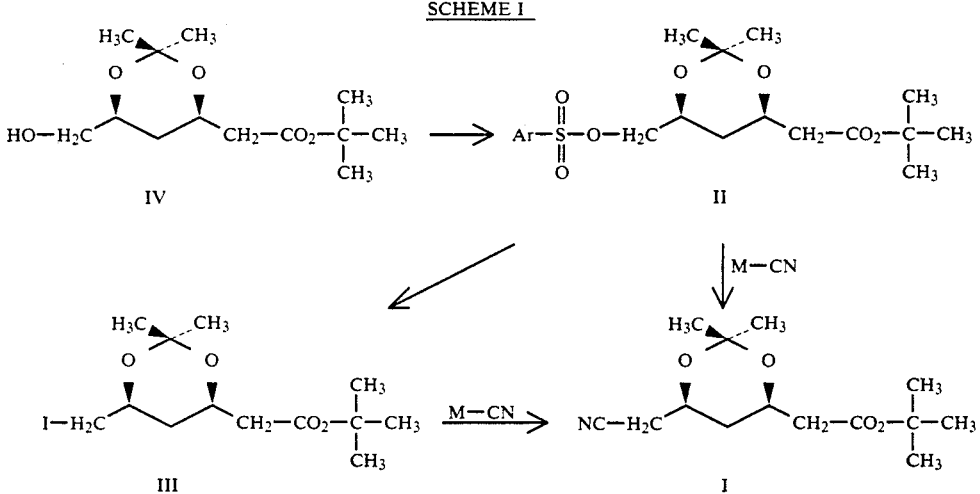

A compound of Formula II wherein Ar is aryl is prepared by treating the compound of Formula IV with a compound of Formula V

wherein X is a halogen such as, for example, chlorine, bromine, iodine, fluorine, and the like, and Ar is as defined above in the presence of a base such as, for example, triethylamine, diisopropylethylamine, 4-dimethylaminopyridine and the like, and a solvent such as, for example, pyridine, toluene, methylene chloride, and the like at about 0° C. to about 40° C. to afford a compound of Formula II. Preferably the reaction is carried out in the presence of triethylamine in methylene chloride at about 0° C. to about 25° C.

The compound of Formula III is prepared by treating a compound of Formula II with an alkali iodide such as, for example, sodium iodide, potassium iodide, and the like in a solvent such as, for example, acetone, 2-butanone, and the like, at about 0° C. to about the reflux temperature of the solvent to afford the compound of Formula III. Preferably the reaction is carried out with sodium iodide in 2-butanone at about 55° C.

The compound of Formula I is prepared by treating either a compound of Formula II, or a compound of Formula III with a compound of Formula VI

M—CN    VI wherein M is an alkali metal, such as, for example, lithium, sodium, potassium and the like, silver or copper (I) (cuprous) optionally in the presence of a quaternary ammonium salt such as, for example, tetrabutylammonium bromide, tetrabutylammonium iodide, benzyltriethylammonium chloride and the like in a solvent such as, for example, ethanol, dimethyl sulfoxide, dimethylformamide, dimethylpropyleneurea, dimethyleneurea, tetramethylurea, N methylpyrrolidinone, tetrahydrofuran, toluene, methylene chloride, and the like, mixtures thereof, as well as any of the aforementioned water-immiscible solvents in combination with water, that is, in a phase transfer procedure using the quaternary ammonium salts as described above at about 0° C. to about the reflux temperature of the solvent to afford a compound of Formula I. Preferably the reaction is carried out in dimethyl sulfoxide at about 20° C. to about 50° C.

The compound of Formula IV is disclosed in European Patent Application 0 319 847. Compounds of Formula V and Formula VI are either known or capable of being prepared by methods known in the art.

Copending U.S. patent application Ser. No. 303,733 discloses the use of (4R-cis)-1,1-dimethylethyl 6-cyanomethyl 2,2-dimethyl-1,3-dioxane-4-acetate in the preparation of (4R-cis)-1,1-dimethylethyl 6-(2-aminoethyl) 2,2-dimethyl-1,3-dioxane-4-acetate, which in turn is used to prepare (2R-trans)-5-(4-fluorophenyl)-2-(1 methylethyl)-N,4-diphenyl-1-[2-(tetrahydro-4-hydroxy 6-oxo-2H-pyran-2-yl)ethyl] -1H-pyrrole-3-carboxamide or the salt of the hydroxy acid, [R-(R*,R*)]-2-(4-fluorophenyl)-β,δ-dihydroxy-5-(1-methylethyl) -3-phenyl-4-[(phenylamino)carbonyl]-1H-pyrrole-1-heptanoic acid calcium salt (2:1), corresponding to the opened lactone ring of the aforementioned compound which is disclosed in U.S. Pat. Nos. 4,647,576 and 4,681,893 as a useful hypolipidemic and hypocholesterolemic agent.

The following examples are illustrative to show the present process, the preparation of starting materials, and the use of (4R-cis)-1,1-dimethylethyl 6-cyanomethyl-2,2-dimethyl-1,3-dioxane-4-acetate obtained by the present process to prepare the key intermediate, (4R-cis)-1,1-dimethylethyl 6-(2-aminoethyl)-2,2-dimethyl-1,3-dioxane-4-acetate, in the synthesis of (2R-trans)-5-(4 fluorophenyl)-2-(1-methylethyl)-N,4-diphenyl-1- [2-(tetrahydro-4-hydroxy-6-oxo-2H pyran-2-yl)ethyl]-1H-pyrrole-3-carboxamide or the salt of the hydroxy acid, [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1), corresponding to the opened lactone ring of the aforementioned compound useful as a hypolipidemic and hypocholesterolemic agent.

EXAMPLE 1

(4R-cis)-1,1-Dimethylethyl 6-cyanomethyl-2,2-dimethyl -1,3-dioxane 4-acetate

Method A

Step A: Preparation of (4R cis)-1,1,-dimethylethyl 6-(4-bromobenzenesulfonyloxymethyl)-2,2-dimethyl-1,3-dioxane -4-acetate To a stirring, 20°–25° C. solution of the (4R-cis)-1,1-dimethylethyl 6-hydroxymethyl-2,2 dimethyl-1,3- dioxane-4-acetate (European Patent Application 0319,847) (10 g, 38 mmol) in methylene chloride) (250 mL) containing triethylamine (10 mL, 72 mmol) is added 4-bromobenzenesulfonyl chloride (15 g, 57.5 mmol). Stirring is continued at 20°–25° C. for 20 hours, the solution is poured onto 250 mL of water and the layers separated. The upper aqueous layer is extracted with 250 mL of methylene chloride and the combined organic layers are washed with 200 mL each of saturated sodium bicarbonate solution, to ensure complete removal of 4-bromobenzenesulfonyl chloride and then saturates sodium chloride solution. Drying the solution with magnesium sulfate and concentration in vacuo gives 26.3 g of the product as a light orange solid.

Step B: Preparation of (4R-cis)-1,1-dimethylethyl 6-cyanomethyl-2,2-dimethyl-1,3-dioxane-4-acetate To a stirring 20°–25° C. solution of the crude 4-bromobenzenesulfonate (24.2 g, 36 mmol) in dimethyl sulfoxide (100 mL) is added sodium cyanide (4.0 g, 81 mmol). The mixture is stirred at 20°–25° C. for 42 hours, a further 2 g (40.5 mmol) of sodium cyanide is added, and stirring continued at 20°–25° C. for 96 hours. The mixture is poured onto 200 mL of water and extracted with 2×200 mL of ethyl acetate. The combined extracts are washed with 100 mL each saturated sodium bicarbonate solution, saturated sodium chloride solution, dried (magnesium sulfate), and concentrated in vacuo to give the product, 11.3 g as a red-brown oil, which solidifies on standing. Column chromatography on flash silica gel and eluting with hexane/ethyl acetate (4:1) gives the product 9.5 g, as pale yellow needles; mp 67.2°–69.7° C. Vapor phase chromatography (VPC): 30 meter DB-5 capillary column 40 to 280° C. at 15° C./min. 18.63 min., 98.35% (area).

Nuclear magnetic resonance ($^1$H-NMR): (CDCl$_3$) δ 1.38 (3H, s), 1.45 (9H, s), 1.75 (1H, m), 2.39 (2H, dq), 2.51 (2H, d), 4.10–4.32 (2H, m).

Optical Rotation: [α]$_D$=1.33° (C=1, CHCl$_3$).

Method B

Step A: Preparation of (4R-cis)-1,1-dimethylethyl 6-(4-chlorobenzenesulfonyloxymethyl)-2,2-dimethyl-1,3-dioxane-4-acetate To a stirring, 0°–5° C. solution of the (4R-cis)-1,1-dimethylethyl 6-hydroxymethyl-2,2-dimethyl-1,3-dioxane-4-acetate (European Patent Application 0319,847) (10 g, 38 mmol) in methylene chloride (250 mL) containing triethylamine (10 mL, 72 mmol) is added 4-chlorobenzenesulfonyl chloride (12.7 g, 60 mmol). Stirring is continued at 0°–5° C. for 2.5 hours and the solution slowly warmed to 20°–25° C. over a period of 2 hours. The solution is poured onto 200 mL of water and the layers separated. The upper aqueous layer is extracted with 200 mL of methylene chloride and the combined organic layers are washed with 200 mL each of saturated sodium bicarbonate solution to ensure complete removal of 4-chlorobenzenesulfonyl chloride and then saturated sodium chloride solution. Drying the solution with magnesium sulfate and concentration in vacuo gives 21.5 g of the product as a pale yellow solid.

Step B: Preparation of (4R-cis)-1,1-dimethylethyl 6-cyanomethyl-2,2 dimethyl-1,3-dioxane-4-acetate To a stirring 20°–25° C. solution of the crude 4-chlorobenzenesulfonate (21.5 g, 38 mmol) in dimethyl sulfoxide (100 mL) is added sodium cyanide (4.0 g, 81 mmol). The mixture is stirred at 20°–25° C. for 40 hours, a further 2 g (40.5 mmol) of sodium cyanide is added and stirring continued at 20°–25° C. for 4.5 hours and 48°–52° C. for 24 hours. The mixture is poured onto 200 mL of water and extracted with 2×250 mL of ethyl acetate. The combined extracts are washed with 100 mL each saturated sodium bicarbonate solution, saturated sodium chloride solution, dried (magnesium sulfate), and concentrated in vacuo to give the product, 11.7 g as a yellow-orange solid. The product is 90% pure (by VPC).

Method C

Step A: Preparation of (4R-cis)-1,1-dimethylethyl 6-(2,5-dichlorobenzenesulfonyloxymethyl)-2,2-dimethyl-1,3-dioxane-4-acetate To a stirring 0°–5° C. solution of the (4R-cis)-1,1-dimethylethyl 6-hydroxymethyl-2,2-dimethyl-1,3-dioxane-4-acetate (European Patent Application 0319,847) (10 g, 38 mmol) in methylene chloride (250 mL) containing triethylamine (10 mL, 72 mmol) is added 2,5-dichlorobenzenesulfonyl chloride (14.7 g, 57.5 mmol). Stirring is continued at 0°–5° C. for 3.5 hours, the solution is poured onto 200 mL of water, and the layers separated. The upper aqueous layer is extracted with 200 mL of methylene chloride and the combined organic layers are washed with 200 mL each of saturated sodium bicarbonate solution to ensure complete removal of 2,5-dichlorobenzenesulfonyl chloride and then saturated sodium chloride solution. Drying the solution with magnesium sulfate and concentration in vacuo gives 24.6 g of the product as a yellow-orange oil.

Step B: Preparation of (4R-cis)-1,1-dimethylethyl 6-cyanomethyl-2,2-dimethyl-1,3-dioxane-4-acetate To a stirring 20°–25° C. solution of the crude 2,5-dichlorobenzenesulfonate (24.6 g, 38 mmol) in dimethyl sulfoxide (100 mL) is added sodium cyanide (4.0 g, 81 mmol). The mixture is stirred at 20°–25° C. for 44 hours, a further 1 g (20 mmol) of sodium cyanide is added and stirring continued at 20°–25° C. for 24 hours. The mixture is poured onto 200 mL of water and extracted with 2×250 mL of ethyl acetate. The combined extracts are washed with 100 mL each saturated sodium bicarbonate solution, saturated sodium chloride solution, dried (magnesium sulfate), and concentrated in vacuo to give the product, 10.7 g as a brown oil, which solidifies on standing. The material is 85% pure (by VPC).

Method D

Step A: Preparation of (4R-cis) 1,1-dimethylethyl 6-(2-nitrobenzenesulfonyloxymethyl)-2,2-dimethyl-1,3-dioxane-4-acetate To a stirring 20°–25° C. solution of the (4R cis)-1,1-dimethylethyl 6-hydroxymethyl-2,2-dimethyl-1,3-dioxane-4-acetate (European Patent Application 0319,847) (10 g, 0.038 mol) in methylene chloride (250 mL) containing triethylamine (7 mL, 0.05 mol) is added 2-nitrobenzenesulfonyl chloride (9.8 g, 0.043 mol). Stirring is continued at 20°–25° C. for 24 hours, a further portion of 2-nitrobenzenesulfonyl chloride (2.0 g, 0.009 mol) is added and the solution stirred for a further 4 hours. The solution is then poured onto 200 mL of water and the layers separated. The upper aqueous layer is extracted with 250 mL of methylene chloride and the combined organic layers are washed with 100 mL each of saturated sodium bicarbonate solution to ensure complete removal of 2-nitrobenzenesulfonyl chloride and then saturated sodium chloride. Drying the solution with magnesium sulfate and concentration in vacuo gives 20.8 g of the product as a green oil.

Step B: Preparation of (4R-cis)-1,1-dimethylethyl 6-cyanomethyl-2,2-dimethyl-1,3-dioxane-4-acetate To a stirring 20°–25° C. solution of the crude 2-nitrobenzenesulfonate (19 g, 35.8 mmol) in dimethyl sulfoxide (100 mL) is added sodium cyanide (4.0 g, 81 mmol). The mixture is stirred at 20°–25° C. for 17 hours, poured onto 200 mL of water, and extracted with 2×200 mL of ethyl acetate. The combined extracts are washed with saturated sodium bicarbonate solution, saturated sodium chloride solution, dried (magnesium sulfate), and concentrated in vacuo to give the product, 10.8 g as a red-brown oil. Column chromatography on flash silica eluting with hexane/ethyl acetate (4:1) gives the product 8.1 g, as a yellow oil which solidifies on standing. The product is 97.4% pure (by VPC).

Method E

Step A: Preparation of (4R-cis)-1,1-dimethylethyl 6-(4-nitrobenzenesulfonyloxymethyl)-2,2-dimethyl-1,3-dioxane-4-acetate To a stirring 20°–25° C. solution of the (4R-cis)-1,1-dimethylethyl 6-hydroxymethyl-2,2-dimethyl-1,3- dioxane-4-acetate (European Patent Application 0319,847) (10 g, 0.038 mol) in methylene chloride (250 mL) containing triethylamine (7 mL, 0.05 mol) is added 4-nitrobenzenesulfonyl chloride (10.5 g, 43 mmol). Stirring is continued at 20°–25° C. for 22 hours, the solution is poured onto 200 mL of water and the layers separated. The upper aqueous layer is extracted with 250 mL of methylene chloride and the combined organic layers are washed with 100 mL each of saturated sodium bicarbonate solution to ensure complete removal of 4-nitrobenzenesulfonyl chloride and then saturated sodium chloride solution. Drying the solution with magnesium sulfate and concentration in vacuo gives 18.7 g of the product as a brown oil which solidifies immediately.

Step B: Preparation of (4R-cis)-1,1-dimethylethyl 6-cyanomethyl-2,2-dimethyl-1,3-dioxane-4-acetate To a stirring 40°–45° C. solution of the crude 4-nitrobenzenesulfonate (12.7 g, 28.5 mmol) in dimethyl sulfoxide (100 mL) is added sodium cyanide (4.0 g, 81 mmol). The mixture is stirred at 40°–45° C. for 1 hour, poured onto 200 mL of water and extracted with 2×200 mL of ethyl acetate. The combined extracts are washed with 100 mL each saturated sodium bicarbonate solution, saturated sodium chloride solution, dried (magnesium sulfate), and concentrated in vacuo to give the product, 8 g as a red-brown oil. Column chromatography on flash silica eluting with hexane/ethyl acetate (4:1) gives the product 2.8 g as a yellow oil which solidifies on standing. The product is 98.0% pure (by VPC).

Method F

Step A: Preparation of (4R-cis)-1,1-dimethylethyl 6-(4-chlorobenzenesulfonyloxymethyl)-2,2-dimethyl-1,3-dioxane-4-acetate To a stirring, 0°–5° C. solution of the (4R-cis)-1,1-dimethylethyl 6-hydroxymethyl-2,2-dimethyl-1,3-dioxane-4-acetate (European Patent Application 0319,847) (10 g, 38 mmol) in methylene chloride (250 mL) containing triethylamine (10 mL, 72 mmol) is added 4-chlorobenzenesulfonyl chloride (12.7 g, 60 mmol). Stirring is continued at 0°–5° C. for 2.5 hours and the solution slowly warmed to 20°–25° C. over a period of 2 hours. The solution is poured onto 200 mL of water and the layers separated. The upper aqueous layer is extracted with 200 mL of methylene chloride and the combined organic layers are washed with 200 mL each of saturated sodium bicarbonate solution to ensure complete removal of 4-chlorobenzenesulfonyl chloride and then saturated sodium chloride solution. Drying the solution with magnesium sulfate and concentration in vacuo gives 21.5 g of the product as a pale yellow solid.

Step B: Preparation of (4R-cis)-1,1-dimethylethyl 6-iodomethyl-2,2-dimethyl-1,3-dioxane-4-acetate To a stirring, 55 to 60° C. suspension of the (4R-cis)-1,1-dimethylethyl 6-(4-chlorobenzene)sulfonyloxy-2,2-dimethyl-1,3-dioxane-4-acetate (21.5 g, 38 mmol) in 2 butanone (100 mL) containing potassium carbonate (10 g, 77 mmol) is added sodium iodide (11.4 g, 77 mmol). Stirring is continued at 55° C. for 30 minutes. The mixture is then heated to a gentle reflux for 18 hours, the solids removed by filtration and the filtrate concentrated to give the product 14 g as an oil.

Step C: Preparation of (4R-cis)-1,1-dimethylethyl 6-cyanomethyl-2,2-dimethyl-1,3-dioxane-4-acetate To a stirring 20° to 25° C. solution of the crude iodide (14 g, 38 mmol) in dimethyl sulfoxide (150 mL) is added sodium cyanide (3.8 g, 77 mmol). The mixture is stirred at 20° to 25° C. for 5 days, poured onto 300 mL water and extracted with 2×250 mL of ethyl acetate. The combined extracts are washed with saturated sodium bicarbonate solution, saturated sodium chloride solution, dried (magnesium sulfate), and concentrated in vacuo to give the product, 10 g as a pale yellow oil which solidifies on standing. The product is 82.4% pure (by VPC).

EXAMPLE 2

(4R-cis)-1,1-dimethylethyl 6-(2-aminoethyl)-2,2-dimethyl-1,3-dioxane-4-acetate

A solution of (4R-cis)-1,1-dimethylethyl 6-cyanomethyl-2,2-dimethyl-1,3-dioxane-4-acetate, (Example 1) 5.63 g (0.048 mol), in 100 mL of methanol saturated with gaseous ammonia is treated with 0.5 g of Raney nickel #30 and hydrogen gas in a shaker at 50 pounds per square inch (psi) and 40° C. After 16 hours, thin layer chromatography indicates no starting nitrile present. The suspension is cooled, filtered through filter aid, and concentrated to an oil. This crude oil is purified by flash chromatography on silica gel with 30:20:1 (ethyl acetate:methanol:ammonium hydroxide) as eluant to give 4.93 g of (4R-cis)-1,1-dimethylethyl 6-(2-aminoethyl) -2,2-dimethyl-1,3-dioxane-4-acetate (98.2 area %) as a clear oil.

200 MHz $^1$H-NMR (CDCl$_3$) 1.0–1.2 (m, 1H), 1.22 (s, 3H), 1.31 (s, 12H), 1.35–1.45 (m, 3H), 2.15 (dd, 1H, J=15.1 Hz, J=6.2 Hz), 2.29 (dd, 1H, J=15.1 Hz, J=7.0 Hz), 2.66 (t, 2H, J=6.6 Hz), 3.82 (m, 1H), 4.12 (m, 1H).

$^{13}$C-NMR (CDCl$_3$, 50 MHz) δ 19.60, 27.96, 30.00, 36.50, 38.25, 39.79, 42.61, 66.08, 67.18, 80.21, 98.35, 169.82.

GC/MS m/e 202, 200, 173, 158, 142, 140, 114, 113, 100, 99, 97, 72, 57.

FTIR (neat) 951.6, 1159.9, 1201.1, 1260.3, 1314.3, 1368.3, 1381.2, 1731.0, 2870.3, 2939.8, 2980.9, 3382.2 cm$^{-1}$.

EXAMPLE 3

(±)4-Fluoro-α-[2-methyl-1-oxopropyl]-γ-oxo-N,β-diphenylbenzenebutaneamide mixture of [R-(R*,R*)], [R(R*,S*)], [R-(R*,S*)], [S-(R*,R*)] and [S-(R*,S*)] isomers Step A: Preparation of 4-Methyl-3 oxo-N-phenyl-2-(phenylmethylene)pentanamide A suspension of 100 kg of 4-methyl-3-oxo-N-phenylpentanamide (Example A) in 660 kg of hexanes is treated with agitation under nitrogen with 8 kg of β-alanine, 47 kg of benzaldehyde, and 13 kg of glacial acetic acid. The resulting suspension is heated to reflux with removal of water for 20 hours. An additional 396 kg of hexanes and 3 kg of glacial acetic acid is added and reflux continued with water removal for 1 hour. The reaction mixture is cooled to 20° to 25° C., and the product is isolated by filtration. The product is purified by slurrying in hexanes at 50°–60° C., cooling, and filtration. The product is slurried twice with water at 20° to 25° C., filtered, and dried in vacuo to yield 110 kg of 4-methyl-3-oxo-N-phenyl-2-(phenylmethylene)pentanamide, mp 143.7°–154.4° C.

Vapor Phase Chromatography (VPC): 30 meter DB-5 capillary column 50° to 270° C. at 15° C./min. 19.33 min., 99.7% (area).

Gas Chromatography/Mass Spectrometry (GC/MC): M/Z 293 [M]$^+$.

Nuclear Magnetic Resonance ($^1$H-NMR): (CDCl$_3$) δ 1.16 (6H, d), 3.30 (1H, quin.), 7.09 (1H, m), 7.28 (5H, m), 7.49 (5H, m), 8.01 (1H, brs).

Step B: Preparation of (±)4-Fluoro-α-[2-methyl-1-oxopropyl]-γ-oxo-N-β-diphenylbenzenebutaneamide mixture of [R-(R*,R*)], [R-(R*,S*)], [S-(R*,R*)] and [S-(R*,S*)] isomers A solution of 17.5 kg of 3-ethyl-5-(2-hydroxyethyl)-4-methylthiazolium bromide in 300 L of anhydrous ethanol is concentrated by distillation of 275 L of the ethanol. Under an argon atmosphere, 100 kg (340 mol) of 4-methyl-3-oxo N-phenyl-2-(phenylmethylene)pentamide, 47.5 L (340 mol) of triethylamine, and 40 L (375 mol) of 4-fluorobenzaldehyde are added. The resulting solution is stirred and heated at 75° to 80° C. for 23 hours. The product begins to form as solid after approximately 1.5 hours but approximately 24 hours is required for essentially complete conversion. The slurry is dissolved in 600 L of isopropanol at 80° C. The resulting solution is slowly cooled and the (±)4-fluoro-α-[2-methyl-1-oxopropyl]-γ-oxo-N,β-diphenyl-benzenebutaneamide mixture of [R-(R*,R*)], [R-(R*,S*)], [S-(R*,R*)] and [S-(R*,S*)] isomers isolated by filtration. Washing the precipitate with isopropanol and drying in vacuo yielded 99 kg of (±)4-fluoro-α-[2-methyl-1-oxopropyl]-γ-oxo-N,β-diphenylbenzenebutanamide mixture of [R-(R*,R*)], [R-(R*,S*)], [S-(R*,R*)], and [S-(R*,S*)] isomers; mp 206.8°–207.6° C.

$^1$H-NMR: (CDCl$_3$) δ 1.03 (3H, d), 1.22 (3H, d), 2.98 (1H, quin.), 4.91 (1H, d, J=11 Hz). 5.51 (1H, d, J=11 Hz), 6.98–7.43 (12H, m), 8.17 (2H, dd), 9.41 (1H, brs).

High Pressure Liquid Chromatography (HPLC): (Acetonitrile:tetrahydrofuran:water) (40:25:55) Econosil C$_{18}$ 5μ 25 cm 1.0 mL/min 254 nm 16.77 min 99.2% (area).

EXAMPLE 4

(2R-Trans)-5-(4-fluorophenyl)-2-(1-methylethyl)-N,4-diphenyl-1 -[2-(tetrahydro-4-hydroxy-6-oxo-2H-pyran-2-yl)ethyl -1-1H-pyrrole-3-carboxamide Method A Step A: Preparation of (4R-cis)-1,1-dimethylethyl 6-[2[2-(4-fluorophenyl)-5-(1-methylethyl)-3-phenyl-4-[(phenylamino)carbonyl]-1H-pyrrol-1-yl]ethyl]-2,2-dimethyl-1,3-dioxane-4-acetate A solution of (4R-cis)-1,1-dimethylethyl 6-(2-aminoethyl) -2,2-dimethyl-1,3-dioxane-4-acetate, (Example 2) 1.36 g (4.97 mmol), and (±)-4-fluoro-α-[2-methyl-1-oxopropyl]-γ-oxo-N,β-diphenylbenzenebutaneamide mixture of [R-(R*,R*)], [R-(R*,S*)], [S-(R*,R*)], and [S-R*,S*)] isomers, (Example 3) 1.60 g (3.83 mmol), in 50 mL of heptane:toluene (9:1) is heated at reflux for 24 hours. The solution is cooled slightly and 15 mL of 2-propanol added. The mixture is allowed to cool to 25° C. and filtered to give 1.86 g of (4R-cis)-1,1-dimethylethyl 6-[2[2-(4-fluorophenyl)-5-(1-methyl-ethyl)-3-phenyl-4-[(phenylamino)carbonyl]-1H-pyrrol-1-yl]ethyl]-2,2-dimethyl-1,3-dioxane-4-acetate as a yellow solid.

$^1$H-NMR (CDCl$_3$, 200 MHz) δ 1–1.7 (m, 5H), 1.30 (s, 3H), 1.36 (s, 3H), 1.43 (s, 9H), 1.53 (d, 6H, J=7.1 Hz), 2.23 (dd, 1H, J=15.3 Hz, J=6.3 Hz), 2.39 (dd, 1H,

J=15.3 Hz, J=6.3 Hz), 3.5–3.9 (m, 3H), 4.0 -4.2 (m, 2H), 6.8–7.3 (m, 14H).

$^{13}$C-NMR (CDCl$_3$, 50 MHz) δ 19.69, 21.60, 21.74, 26.12, 27.04, 28.12, 29.95, 36.05, 38.10, 40.89, 42.54, 65.92, 66.46, 80.59, 98.61, 115.00, 115.34, 115.42, 119.52, 121.78, 123.36, 126.44, 128.21, 128.31, 128.52, 128.75, 130.43, 133.01, 133.17, 134.69, 138.38, 141.47, 159.72, 164 64, 169.96.

Step B: Preparation of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (4R-cis)-1,1-dimethylethyl 6-[2[2-(4-fluorophenyl)-5-(1-methylethyl)-3-phenyl -4-[(phenylamino)carbonyl]-1H-pyrrol-1-yl]ethyl]2,2-dimethyl-1,3-dioxane-4-acetate, 4.37 g (6.68 mmol), is dissolved in 200 mL of tetrahydrofuran and 15 mL of 10% hydrochloric acid solution is added, and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for 3 hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred 2 hours, concentrated in vacuo, and dissolved in 3.0 mL of toluene. (2R-trans)-5-(4-fluorophenyl)-2-(1-methylethyl)-N,4-diphenyl-1-[2-tetrahydro-4 hydroxy 6-oxo-2H-pyran-2-yl)ethyl]-1H-pyrrole-3 carboxamide (3.01 g) is isolated in two crops.

Method B

A solution of (4R-cis)-1,1-dimethylethyl 6-(2-aminoethyl) -2,2-dimethyl-1,3-dioxane-4-acetate, (Example 2) 2.56 g (9.36 mmol), and (±)-4-fluoroα-[2-methyl-1-oxopropyl]-γ-oxo-N,β-diphenylbenzenebutaneamide mixture of [R-(R*,R*)], [R-(R*,S*)], [S-(R*,R*)], and [S (R*,S*)] isomers (Example 3), 3.00 g (7.20 mmol), in 60 mL of heptane:toluene (9:1) is heated at reflux for 24 hours. The solution is cooled and poured into 300 mL of tetrahydrofuran and 150 mL of saturated ammonium chloride in water. The layers are separated and the organic layer is added to 15 mL of 10% hydrochloric acid solution and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for 3 hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred 2 hours, concentrated in vacuo, and dissolved in 3.0 mL of toluene. (2R trans)-5 (4-fluorophenyl)-2 (1-methylethyl) -N,4-diphenyl-1-[2-(tetrahydro-4-hydroxy-6-oxo-2H-pyran-2-yl)ethyl]-1H-pyrrole-3-carboxamide (2.92 g) is isolated in two crops.

PREPARATION OF STARTING MATERIALS

EXAMPLE A

4-Methyl-3-oxo-N-phenylpentamide

A three-necked, 12-L round-bottom flask equipped with a mechanical stirrer, a thermometer, and set up for distillation is charged with 2.6 L of toluene, 1.73 kg (12 mol) of methyl 4-methyl-3-oxopentanoate and 72 g (1.18 mol) of ethylenediamine. The mixture is heated to 80° C. and charged with 0.49 kg of aniline. The mixture is brought to reflux and distillation started. After 40 minutes a further 0.245 kg of aniline is charged and at 40-minute intervals a further two portions of aniline (0.245 and 0.25 kg) are charged. Distillation is continued for a further one to five hours until a total of 985 mL of solvent is removed. The solution is stirred at room temperature for 16 hours and a further 550 mL of solvent is removed by vacuum distillation (using approximately 85 mm Hg). The mixture is cooled and 2 L of water is charged to provide an oil. The mixture is warmed to 40° C. and a further 1.0 L of water is charged. Seven hundred milliliters of toluene-water mixture is removed by vacuum distillation (approximately 20 mm Hg). Two liters of water is charged and the mixture is allowed to stand for 10 days. The product is isolated by filtration and washed with three portions of hexane. Drying in vacuo gives 1.7 kg of 4-methyl-3-oxo-N-phenylpentanamide as a hydrate; m.p. 46.5°–58.8° C.

HPLC: 98.8%—retention time 3.56 minutes. 65/35 acetonitrile/water on a dry basis.

VPC: 87.6%—retention time 12.43 minutes, also 10.8% aniline (decomposition).

We claim:
1. A compound of Formula

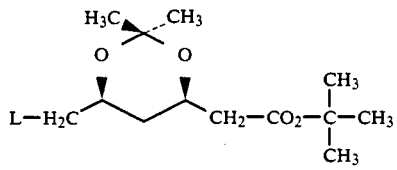

wherein L is iodo or

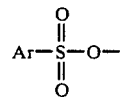

wherein
Ar is phenyl substituted by one to two substituents selected from halogen or nitro.
2. A compound according to claim 1 which is selected from the group consisting of:
(4R-cis)-1,1-dimethylethyl 6-(4-bromobenzene) sulfonyloxymethyl-2,2-dimethyl-1,3-dioxane-4-acetate;
(4R-cis)-1,1-dimethylethyl 6-(4-chlorobenzene) sulfonyloxymethyl-2,2-dimethyl-1,3-dioxane-4-acetate;
(4R-cis)-1,1-dimethylethyl 6-(2,5-dichlorobenzene) sulfonyloxymethyl-2,2-dimethyl-1,3-dioxane-4-acetate;
(4R-cis)-1,1-dimethylethyl 6-(2-nitrobenzene) sulfonyloxymethyl-2,2-dimethyl-1,3-dioxane-4-acetate;
(4R-cis)-1,1-dimethylethyl 6-(4-nitrobenzene) sulfonyloxymethyl-2,2-dimethyl-1,3-dioxane-4-acetate; and
(4R-cis)-1,1-dimethylethyl 6-iodomethyl-2,2-dimethyl-1,3-dioxane-4-acetate.

* * * * *